US006990225B2

(12) United States Patent
Tanaka et al.

(10) Patent No.: US 6,990,225 B2
(45) Date of Patent: Jan. 24, 2006

(54) INSPECTION METHOD OF PHOTO MASK FOR USE IN MANUFACTURING SEMICONDUCTOR DEVICE

(75) Inventors: Satoshi Tanaka, Kawasaki (JP); Soichi Inoue, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 731 days.

(21) Appl. No.: 10/131,036

(22) Filed: Apr. 25, 2002

(65) Prior Publication Data

US 2002/0192578 A1  Dec. 19, 2002

(30) Foreign Application Priority Data

Apr. 26, 2001  (JP) .............................. 2001-129246

(51) Int. Cl.
*G06K 9/00* (2006.01)
*G01N 21/00* (2006.01)

(52) U.S. Cl. .................... 382/144; 382/145; 356/237.4
(58) Field of Classification Search ................ 382/141, 382/143, 144–152; 348/86, 87, 125, 126; 356/237.1, 237.4, 237.5, 400; 700/95; 250/559.34
See application file for complete search history.

(56) References Cited

U.S. PATENT DOCUMENTS 4,871,257 A * 10/1989 Suzuki et al. ............... 356/400
6,760,101 B2 * 7/2004 Sato et al. ............... 356/237.4

FOREIGN PATENT DOCUMENTS

JP  2000-122265  4/2000

OTHER PUBLICATIONS

Chen, J. F. et al., "CD Error Sensitivity to "Sub-Killer" Defects at $K_1$ Near 0.4", SPIE, vol. 3677, pp. 722-733, (Mar. 1999).
Pati, Y. C. et al., "Phase-Shifting Masks for Microlithography: Automated Design and Mask Requirements", J. Opt. Soc. Am. A, vol. 11, No. 9, pp. 2438-2452, (Sep. 1994).
Gans, F. et al., "Printability and Repair Techniques for DUV Photomasks", SPIE, vol. 3236, pp. 136-141, (Sep. 1997).
Pettibone, D. et al., "Wafer Printability Simulation Accuracy Based on UV Optical Inspection Images of Reticle Defects", SPIE, vol. 3677, pp. 711-720, (Mar. 1999).

* cited by examiner

*Primary Examiner*—Vikkram Bali
(74) *Attorney, Agent, or Firm*—Finnegan, Henderson, Farabow, Garrett & Dunner, LLP.

(57) ABSTRACT

An inspection method of a mask pattern for exposure comprises using substantially the same inspection wavelength as an exposure wavelength for use in the exposure apparatus and using a detection optical system of the inspection apparatus having a numerical aperture larger than a numerical aperture of a projection optical system of the exposure apparatus to prepare image data of the mask pattern for exposure using the detection optical system and reconstructing low-ordered diffracted light distribution obtained from the mask pattern for exposure by using the image data based on information of the detection optical system. The inspection method comprises using transfer simulation in the projection optical system of the exposure apparatus to obtain an image intensity distribution obtained on a wafer from the low-ordered diffracted light distribution and judging acceptance/rejection of inspection based on the obtained image intensity distribution.

10 Claims, 9 Drawing Sheets

FIG. 4A Black defect (100nm)
Phase difference
180 degrees
Transmittance 6%

FIG. 4B Black defect (200nm)
Phase difference
180 degrees
Transmittance 6%

FIG. 4C Black defect (300nm)
Phase difference
180 degrees
Transmittance 6%

FIG. 5A Black defect (100nm)
Phase difference
90 degrees
Transmittance 6%

FIG. 5B Black defect (200nm)
Phase difference
90 degrees
Transmittance 6%

FIG. 5C Black defect (300nm)
Phase difference
90 degrees
Transmittance 6%

INSPECTION METHOD OF PHOTO MASK FOR USE IN MANUFACTURING SEMICONDUCTOR DEVICE

CROSS-REFERENCE TO RELATED APPLICATIONS

This application is based upon and claims the benefit of priority from the prior Japanese Patent Application No. 2001-129246, filed Apr. 26, 2001, the entire contents of which are incorporated herein by reference.

BACKGROUND OF THE INVENTION

1. Field of the Invention

The present invention relates to an inspection method of a mask pattern formed on a photo mask for exposure for use in manufacturing a semiconductor device, particularly to an inspection method of a mask pattern for more strictly judging whether a defect of the mask pattern found by inspection is allowable.

2. Description of the Related Art

In recent years, semiconductor devices such as LSI have been formed to be finer, and accordingly a size of a mask pattern formed on a photo mask for exposure for use in manufacturing the semiconductor device also needs to be below 1 $\mu$m. Moreover, phenomena in which the pattern cannot be transferred onto a wafer as designed, that is, optical proximity effects (OPE) have also clearly existed. Therefore, a technique of using the corrected mask pattern to finish the transferred shape in accordance with a desired design pattern, that is, optical proximity correction (OPC) has been required. When this technique is introduced, it is possible to suppress a CD (Critical Dimension) variation on the wafer. Thereby, even a finer pattern can faithfully be finished on the wafer as designed. As a result, conversely, a necessary shape as the mask pattern actually formed on the photo mask for exposure is largely different from a desired pattern shape (design value) on the wafer. In this photo mask for exposure, it has become difficult to inspect defects of the mask pattern.

In an inspection apparatus for inspecting presence/absence of the defects in the mask pattern, two systems, that is, an optical system and EB system are generally used as measurement systems. As inspection techniques, a system (die-to-die) for detecting differences among a plurality of chips formed on the same photo mask for exposure, and a system (die-to-database (DB)) for detecting the mask pattern formed on the photo mask for exposure and a difference from data of the mask pattern are used. The existing problem lies in that it is very difficult to clarify specification for setting an allowable difference. That is, when the specification can be clarified from a viewpoint of mask preparation, a finished product can be manufactured without correcting the defects having a value not more than a certain allowable value, and it is possible to enhance yield of mask supply. However, it is difficult to set the allowable value in situations.

To solve the problem, the masks for exposure (program defect masks) produced using a plurality of data called program defects including a defect dimension and defect generation position are prepared, a defect transfer test from the mask to wafer using exposure apparatus is carried out for each type of defect, and it is judged whether the masks could be applied for making LSI chips or not.

Moreover, a technique for determining the size of the defect having the allowable value from the judgment result has been used. In recent years, the result of the transfer test conducted on the wafer using the mask for exposure prepared by the program defect has also been reported (Proc. SPIE Vol. 3677 pl. 722–733, J. Fung Chen, et al.). Moreover, in recent years, this report has been complemented by introducing a lithography simulation technique. In simulation, the data such as the defect dimension, and generation position are changed, the transfer test is carried out, and the allowable defect dimension, and the like of the mask for exposure are obtained.

Moreover, in recent years, a technique of directly diverting a mask image obtained by an inspection apparatus to transfer simulation and judging whether the mask could be applied for making LSI chips or not has also been reported (Proc. SPIE Vol. 3677 pl. 711–720 Donald Pettibone, et al., Wafer Printability Simulation Accuracy Based on UV Optical Inspection Images of Reticle Defects). Furthermore, a technique of observing the mask for exposure in an apparatus having a resolution characteristic equal to that of an exposure optical system and inspecting the transfer of the defect on the wafer (defect transfer characteristic) has also been proposed (Proc. SPIE Vol. 3236 pl. 136–141, Fritz Ganz, et al.).

However, these have some problems.

It is difficult to generalize the technique of preparing the program defect mask, carrying out the transfer test, and evaluating the mask because of limited types of defects. Moreover, it is necessary to set the defect size to be detected, that is, so-called inspection sensitivity for each type of the defect, and this technique is remarkably complicated and specialized.

Furthermore, for the technique of judging the transfer characteristic by the simulation, even when the method of extracting a contour from the mask pattern is used, it is difficult to evaluate an influence of topography effect by a micro pattern or a "gray tone" defect whose phase or transmittance is not equal to the mask Qz(quatz) substrate nor pattern itself (opaque or attenuated).

Figure 3:
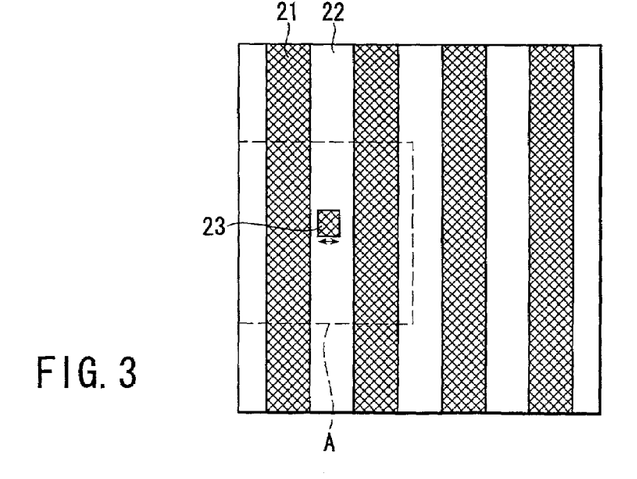
FIG. 3 is a plan view of the mask pattern in the photo mask for exposure.
Figure 4A:
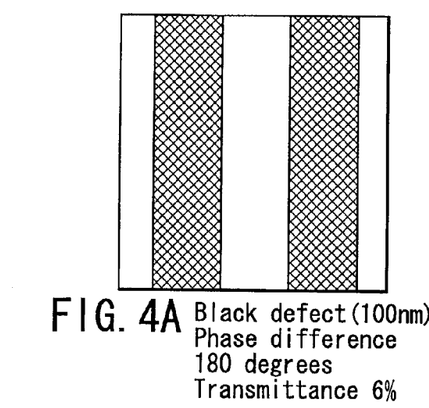
FIGS. 4A, 4B, 4C, 5A, 5B, 5C, 6A, 6B, 6C, 7A, 7B and 7C are enlarged plan views of a region A in the mask pattern shown in FIG. 3.
Figure 4B:
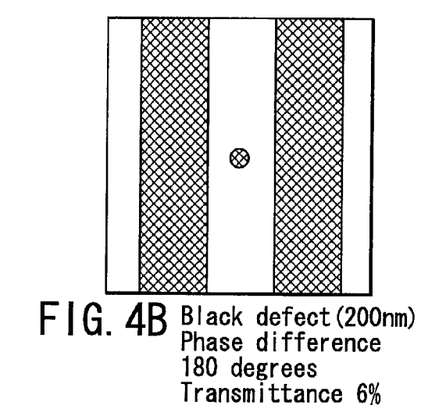
Figure 4C:
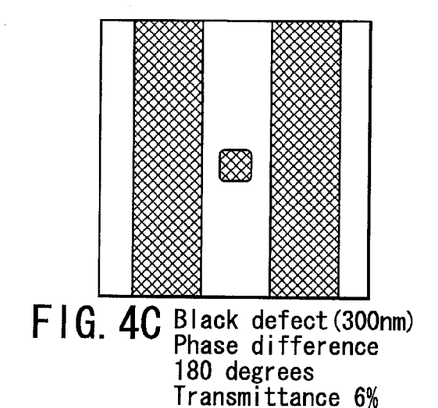
Figure 5A:
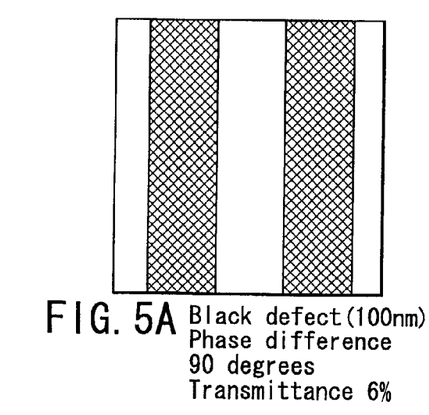
Figure 5B:
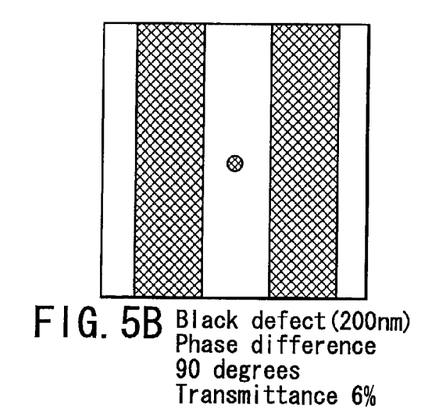
Figure 5C:
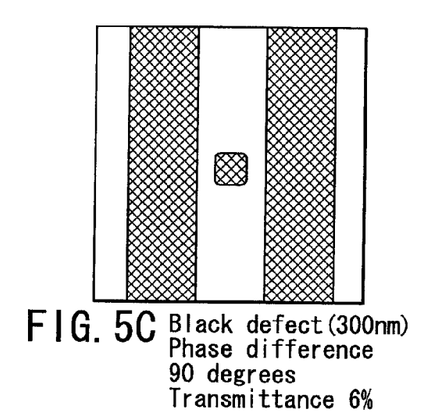
Figure 6A:
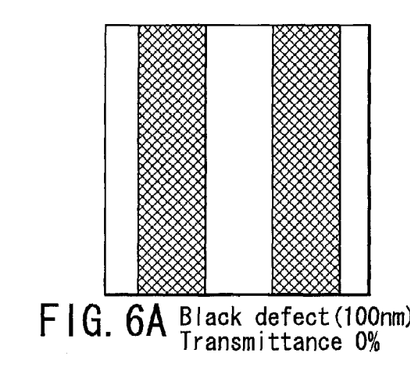
Figure 6B:
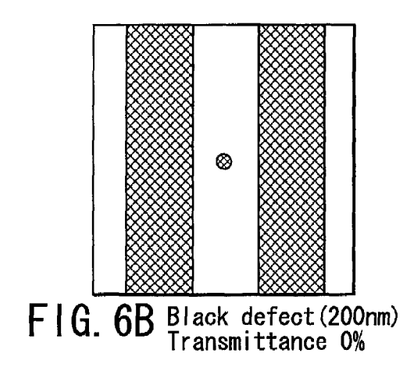
Figure 6C:
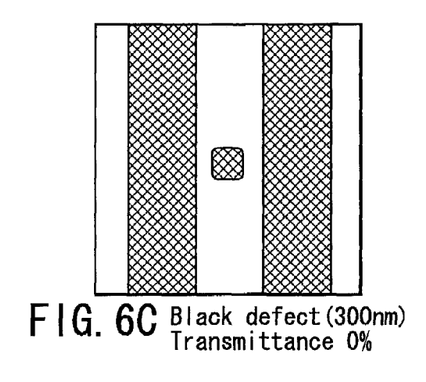
Figure 7A:
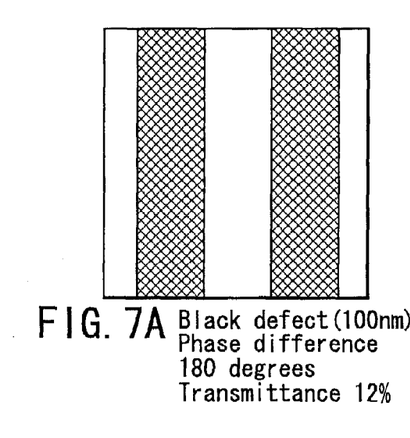
Figure 7B:
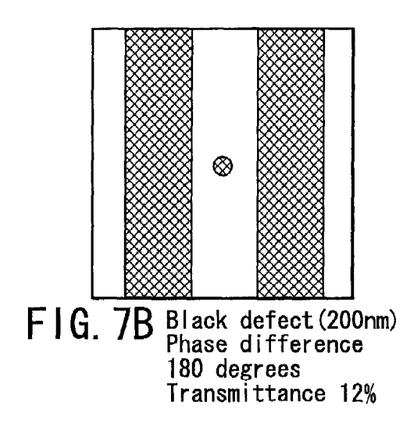
Figure 7C:
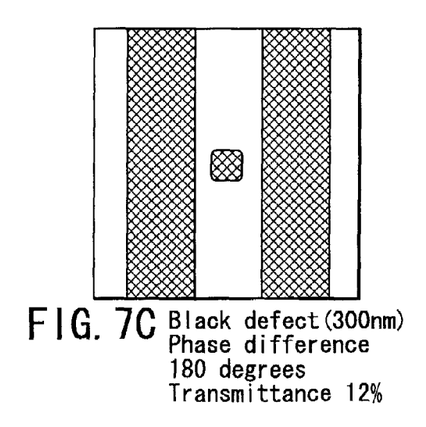

The above-described respect will concretely be described with reference to FIGS. 3 to 11. FIG. 3 is a plan view of the mask pattern formed on the mask for exposure. As shown in FIG. 3, in the mask for exposure, a plurality of linear halftone portions 21 and space portions 22 are arranged on a substrate formed of quartz, and the like. The halftone portions 21 and space portions 22 form a line and space (L&S) pattern. The mask for exposure is assumed as its magnification factor from wafer to mask is 4×, and the mask for exposure is used to manufacture a pattern having a line width of 0.15 $\mu$m and space width of 0.15 $\mu$m on the wafer. It is assumed that a defect 23 exists in a region A of the line and space pattern on the mask for exposure.

FIGS. 4A, 4B, 4C, 5A, 5B, 5C, 6A, 6B, 6C, 7A, 7B and 7C are enlarged views showing a binarized image intensity distribution obtained by the detection optical system, which is assumed to assemble an inspection system of mask. when the size, phase, and transmittance of the defect 23 present in the region A are changed. Assumed optical conditions of the detection optical system and conditions of the mask for exposure as an object to be measured are as follows.

An inspection wavelength for use in the detection optical system=248 nm, numerical aperture (NA)=0.9, coherence factor ($\sigma$)=0.8, a halftone phase shift mask is used, and threshold value for use in binarization=0.1769. Additionally, the threshold value is a value obtained when the halftone portions do not exist, the influence of diffraction is not exerted, and an opening transmitted light of the mask for exposure is normalized as unit (1).

Additionally, the defects 23 shown in FIGS. 4A–4C, 5A–5C, 6A–6C and 7A–7C are black defects which have sizes of 100 nm, 200 nm, and 300 nm. A phase difference is 180 degrees in FIGS. 4A–4C, and 90 degrees in FIGS. 5A–5C, and the transmittance is 0% in FIGS. 6A–6C, and 12% in FIGS. 7A–7C.

Figure 8:
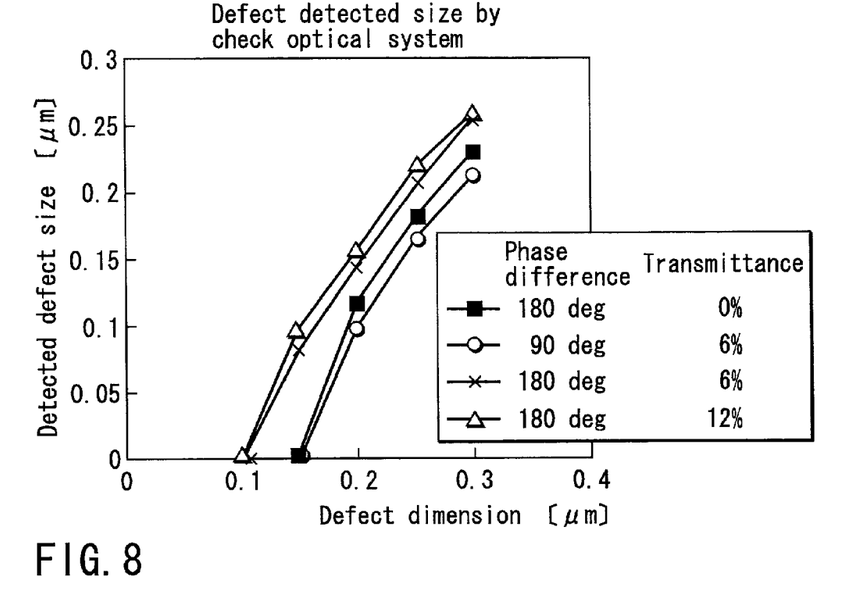
FIG. 8 is a characteristic diagram showing a relation between a defect size detected by an inspection optical system (ordinate) and a defect dimension of the mask pattern (abscissa).

FIG. 8 is a characteristic diagram showing a relation between the defect detected size by the inspection optical system (ordinate) ($\mu$m) and the dimension of the defect present in the mask for exposure (abscissa) ($\mu$m). That is, FIG. 8 shows a relation between the size of the defect obtained by the detection optical system and the size of the defect on the actual reticle (mask). In FIG. 8, -x- corresponds to FIGS. 4A–4C, -○- corresponds to FIGS. 5A–5C, -■- corresponds to FIGS. 6A–6C, and -△- corresponds to FIGS. 7A–7C.

Figure 9:
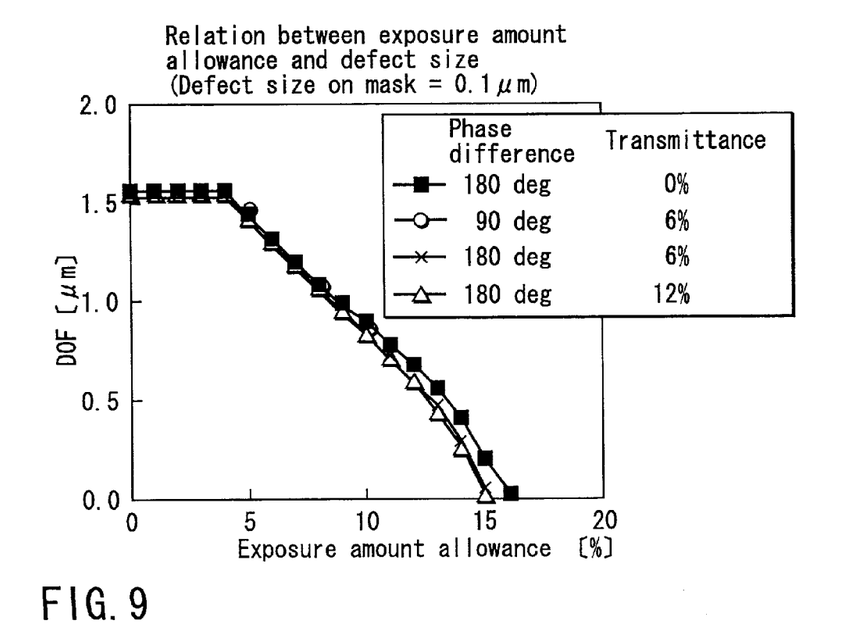
FIGS. 9, 10 and 11 are a characteristic diagram showing a relation between a depth of focus (DOF) (ordinate) and an exposure amount allowance (abscissa).
Figure 10:
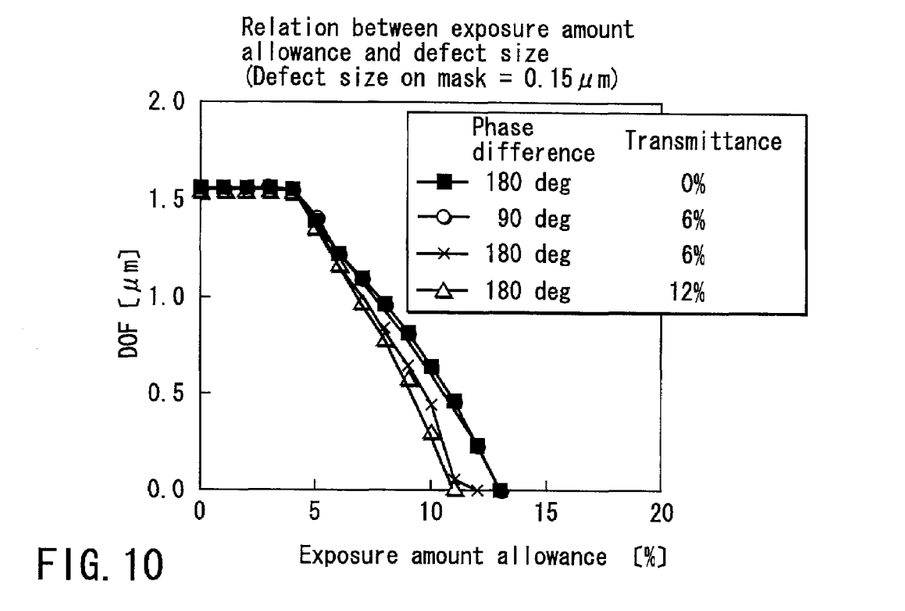
Figure 11:
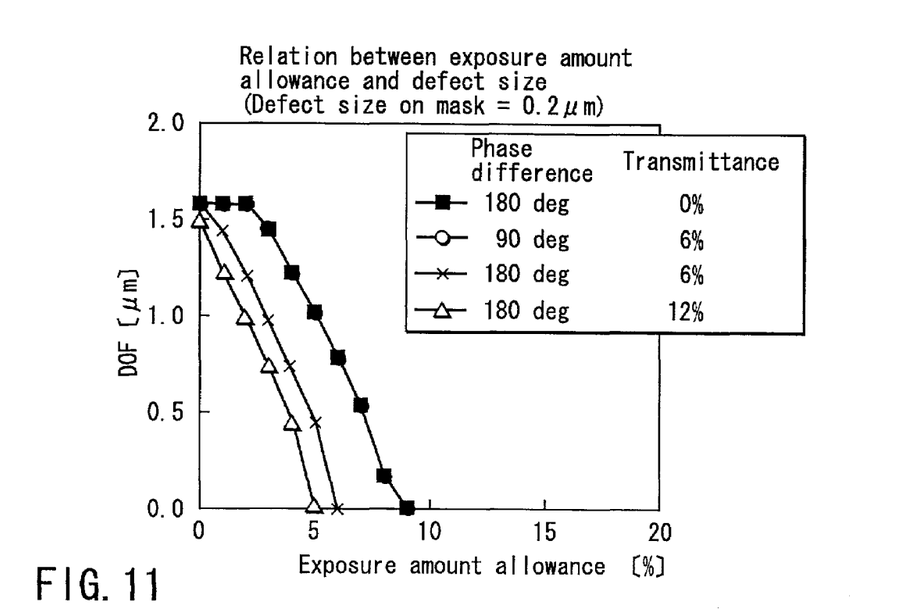

FIGS. 9 to 11 are characteristic diagrams showing a relation between a depth of focus (DOF) ($\mu$m) (ordinate) and an exposure amount allowance (%) (abscissa), and show the deterioration of the exposure amount allowance of the resist dimension on the wafer with respect to the defect on the mask for exposure. In the figures, similarly as FIG. 8, -x- corresponds to FIGS. 4A–4C, -○- corresponds to FIGS. 5A–5C, -■- corresponds to FIGS. 6A–6C, and -△- corresponds to FIGS. 7A–7C. Moreover, in FIG. 9, the defect size on the mask for exposure is 0.1 $\mu$m. In FIG. 10, the defect size on the mask for exposure is 0.15 $\mu$m. In FIG. 11, the defect size on the mask for exposure is 0.2 $\mu$m.

Figure 12:
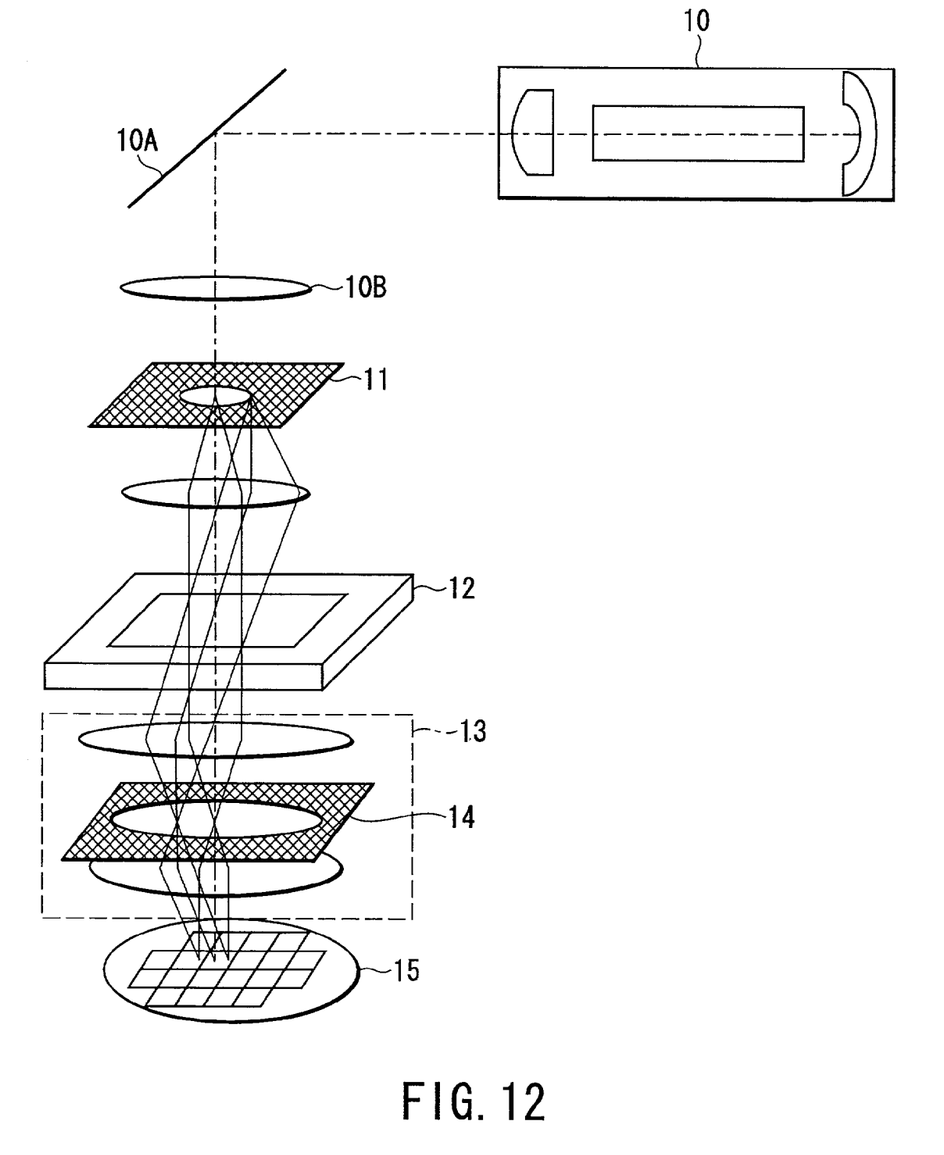
FIG. 12 is a schematic perspective view of an exposure apparatus for use in the embodiment of the present invention and a conventional example.

Exposure conditions for use during the transfer simulation onto the wafer are hereinafter shown. FIG. 12 is a schematic perspective view of an exposure apparatus for use in the embodiment of the present invention and in a conventional example.

The exposure conditions include the exposure wavelength=248 nm, numerical aperture (NA)=0.68, coherence factor ($\sigma$)=0.75, and annular illumination with its center-shielding ratio is 2/3.

Here, as a model for obtaining a resist dimension, a technique of convoluting/integrating Gaussian function with respect to an optical image I(x), and defining the dimension with the threshold value corresponding to an exposure amount is used.

$$Ig(x) = I(x) \ (x) g(x) \tag{7}$$
$$= 1/(\sqrt{(\pi)} \cdot \Delta L) \int I(x-x')\exp(-x'^2/\Delta L^2)dx'$$

Here, the equation was calculated assuming $\Delta L$=60 nm, and (x) represents convolution/integration (x is put in ○ in an actual symbol).

For example, assuming that a necessary allowance is the exposure amount allowance of 10% or more, and the depth of focus (DOF) is 0.5 $\mu$m or more, as shown in FIG. 10, when the size of the defect on the mask for exposure is 0.15 $\mu$m, a defect having a phase of 180 degrees and transmittance of 0%, and a defect having a phase of 90 degrees and transmittance of 6% are accepted. However, the other defects are rejected. As shown in FIG. 8, the size of the defect detected by the corresponding inspection apparatus is 0 for the accepted defect, and is of the order of 0.08 to 0.1 $\mu$m for the rejected defect.

As shown in FIG. 11, when the size of each defect on the mask for exposure is 0.2 $\mu$m, all the defects are rejected. When these defects are seen from the viewpoint of the exposure allowance, there is little difference between the defect having a phase of 180 degrees and transmittance of 0% and the defect having a phase of 90 degrees and transmittance of 6%. However, both defect sizes are detected to be different from each other by about 20 nm by the inspection optical system.

When the transmittance and phase differ in this manner, a correlation between the allowable defect size and the size obtained by the detection optical system is deteriorated. Therefore, the allowable defect size cannot but be set to be in a strict direction. As a result, even the mask for exposure which can originally be shipped is judged to be NG, and production yield in manufacturing the mask for exposure decreased.

It is also possible to use the inspection apparatus which has a resolution characteristic (NA/$\lambda$/$\sigma$) equal to that of the exposure apparatus. In this case, the characteristics (such as aberration) inherent in the actual exposure apparatus differ in many cases, and it is difficult to remove the influence.

As described above, the defect dimension accepted in the conventional inspection technique cannot but be set to the allowable value which has a considerable allowance. As a result, it is difficult to supply the photo mask for exposure within the allowable value.

BRIEF SUMMARY OF THE INVENTION

According to an aspect of the present invention, there is provided an inspection method of a mask pattern for exposure for use in an exposure apparatus for manufacturing a semiconductor device, comprising: using substantially the same inspection wavelength as an exposure wavelength for use in the exposure apparatus, using a detection optical system of the inspection apparatus having a numerical aperture larger than the numerical aperture of a projection optical system of the exposure apparatus, and preparing image data of the mask pattern for exposure using the detection optical system; reconstructing a low-ordered diffracted light distribution obtained from the mask pattern for exposure by using the image data based on information of the detection optical system; using transfer simulation in the projection optical system of the exposure apparatus, and obtaining an image intensity distribution obtained on a wafer from the low-ordered diffracted light distribution; and judging acceptance/rejection of inspection based on the obtained image intensity distribution.

DETAILED DESCRIPTION OF THE INVENTION

An embodiment of the present invention will be described hereinafter with reference to the drawings.

First, the embodiment will be described with reference to FIGS. 1, 2 and 12 to 15.

Figure 1:
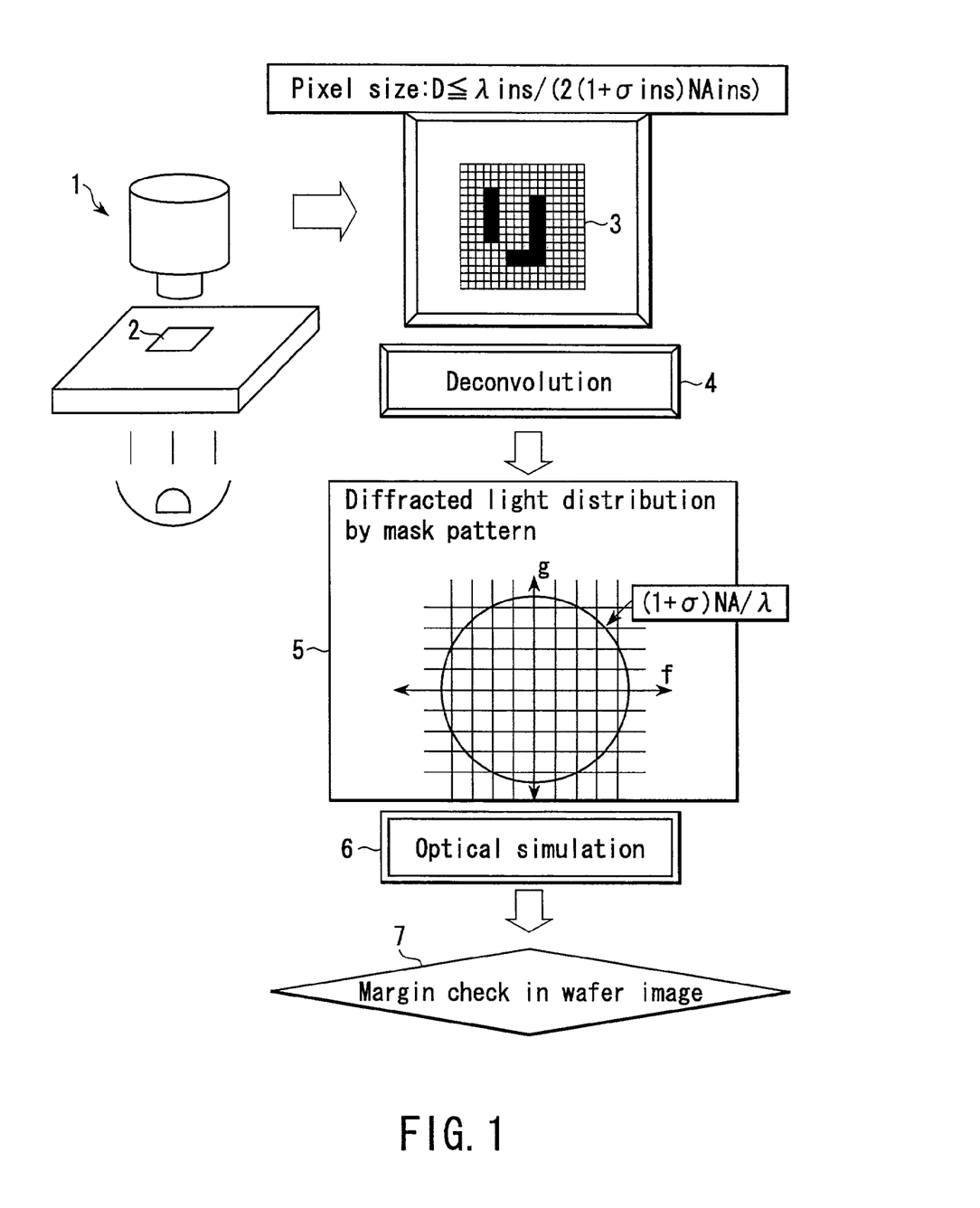
FIG. 1 is a process diagram showing a pattern inspection method of a photo mask for exposure for use in manufacturing a semiconductor device according to an embodiment of the present invention.
Figure 2:
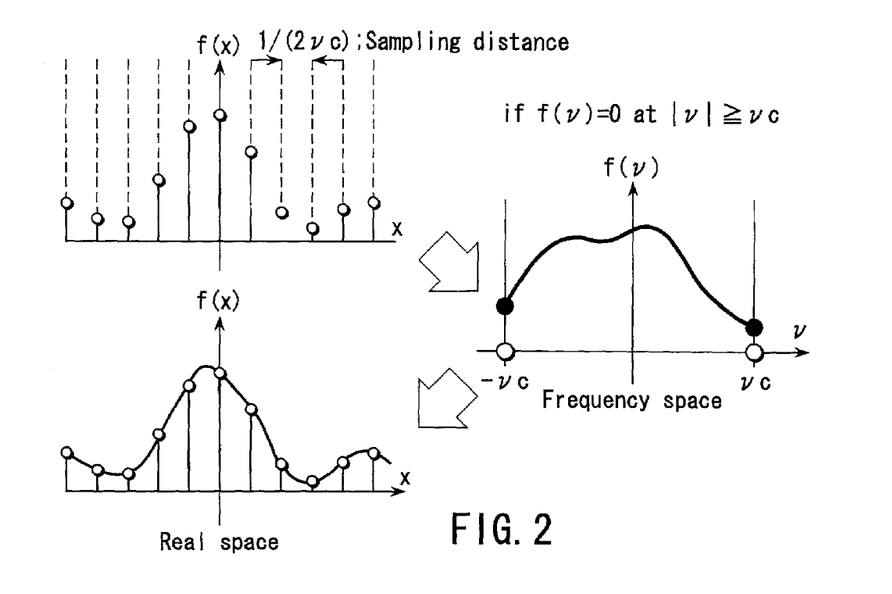
FIG. 2 is a characteristic diagram showing a sampling theorem for use in the embodiment of the present invention.
Figure 13:
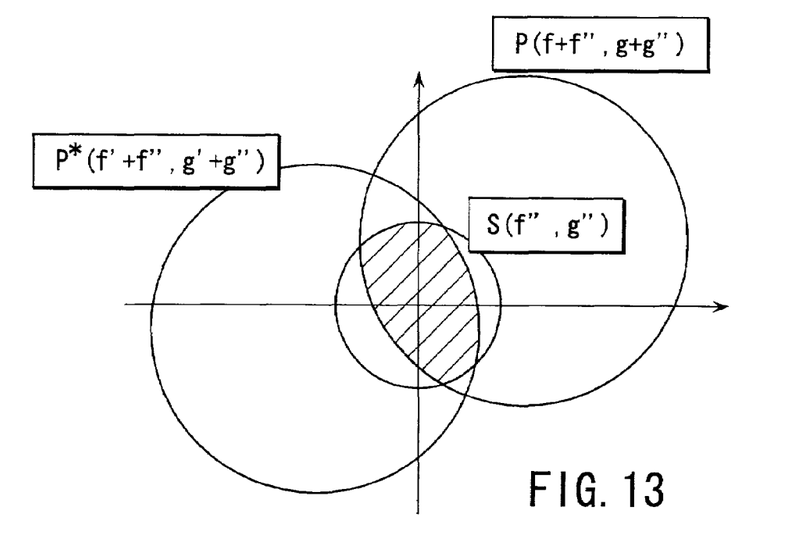
FIG. 13 is a characteristic diagram showing an integration region for obtaining TCC of equation (8) representing a mask pattern image obtained by an inspection optical system according to the embodiment of the present invention.
Figure 14:
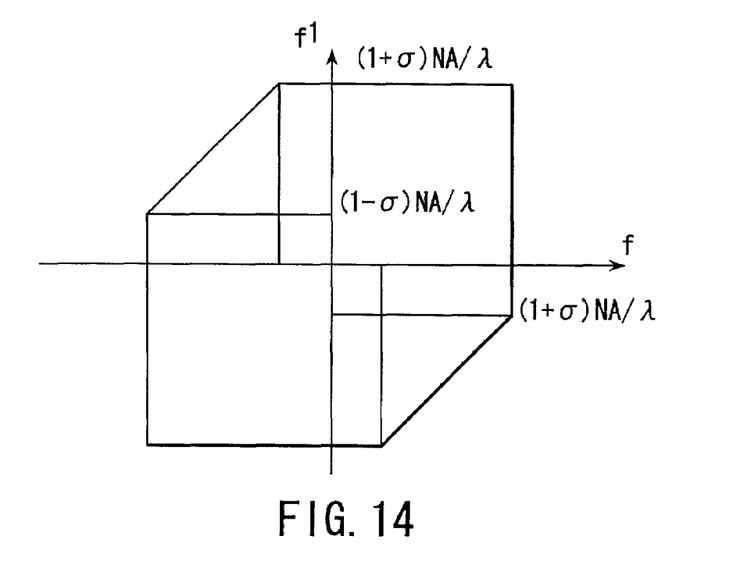
FIG. 14 is a characteristic diagram showing a band of TCC (f,0;f',0) according to the embodiment of the present invention.
Figure 15:
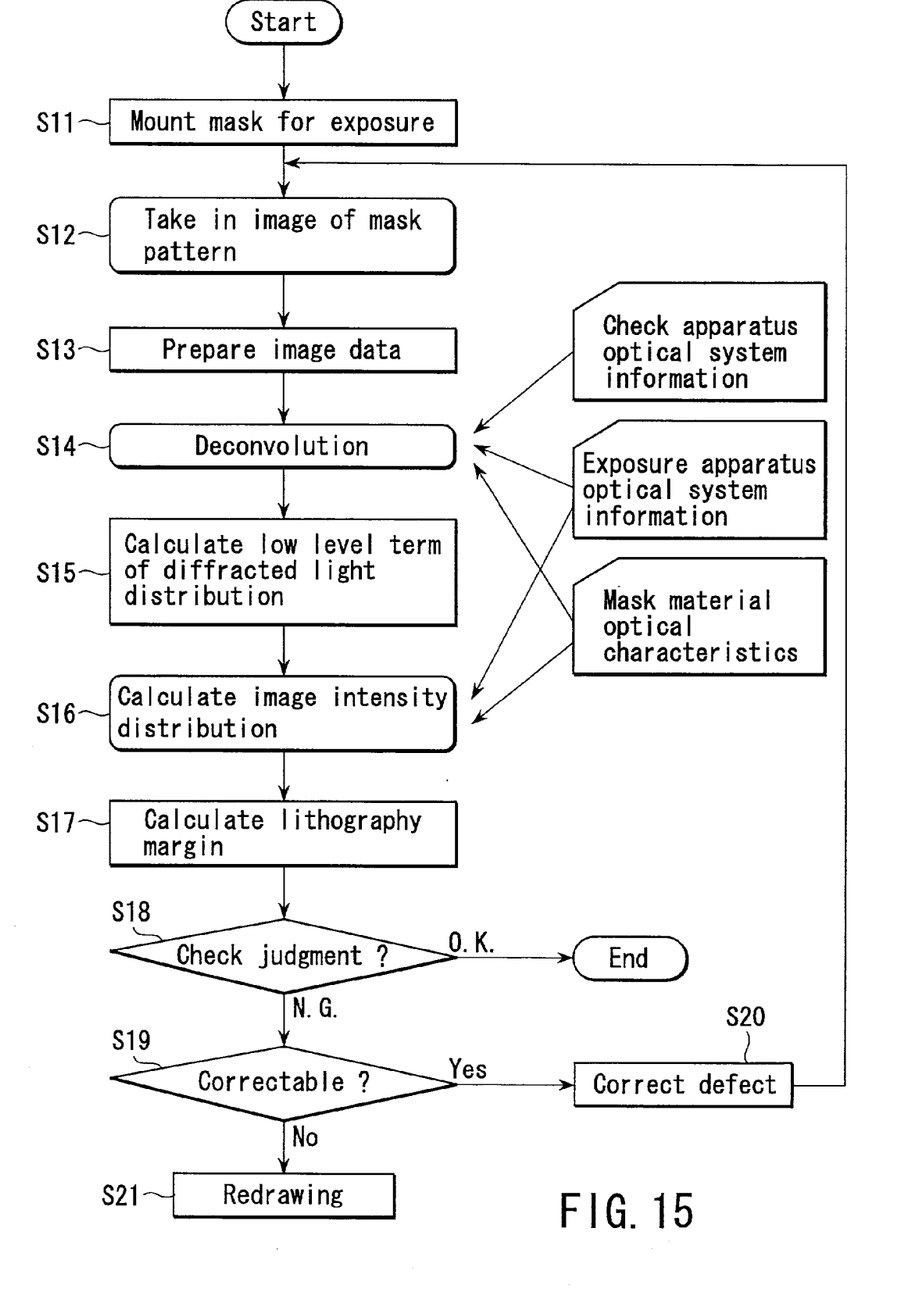
FIG. 15 is a flowchart showing an inspection method of a photo mask for exposure according to the embodiment of the present invention.

FIG. 1 is a diagram showing steps of a pattern inspection method of a photo mask for exposure for use in manufacturing a semiconductor device according to the embodiment of the present invention. FIG. 2 is a characteristic diagram showing a sampling theorem for use in the pattern inspection method of the embodiment. FIG. 12 is a perspective view of an exposure apparatus for use in manufacturing the semiconductor device of the embodiment. FIG. 13 is a characteristic diagram showing an integration region for obtaining a transmission cross coefficient (TCC) of equation (8) representing a mask pattern image obtained by an inspection optical system of the embodiment. FIG. 14 is a characteristic diagram showing a band of TCC (f,0;f',0) of the embodiment. FIG. 15 is a flowchart showing the pattern inspection method of the embodiment. In the embodiment of the present invention, the mask pattern image formed by an optical inspection apparatus is used.

The pattern inspection method of the photo mask for exposure for use in manufacturing the semiconductor device according to the embodiment of the present invention will be described with reference to FIG. 1. Substantially the same inspection wavelength as an exposure wavelength for use in the exposure apparatus is used, and a mask for exposure 2 is disposed in a detection optical system of an inspection apparatus 1 which has a numerical aperture larger than that of a projection optical system of the exposure apparatus. Image data 3 of the mask pattern formed in the mask for exposure 2 is prepared by the detection optical system A Low-ordered diffracted light distribution obtained from the mask pattern formed on the mask for exposure 2 is obtained from the image data 3 of the mask pattern obtained in this manner based on the information of the detection optical system by deconvolution 4 (5).

Subsequently, a mask pattern image obtained when the mask pattern is transferred onto a wafer in the optical system of the exposure apparatus is calculated by optical simulation 6 in which the low-ordered obtained diffracted light distribution is used. Moreover, an image intensity distribution obtained on the wafer is obtained by the mask pattern image. Thereafter, it is judged based on the image intensity distribution whether the mask pattern formed on the mask for exposure 2 is accepted/rejected (7). That is, margins of the depth of focus, exposure dose latitude, and the like in the image intensity distribution (wafer image) are obtained, and each obtained margin is compared with a predetermined reference.

FIG. 15 is a flowchart showing a method of correcting the mask pattern on the mask for exposure by the inspection method shown in FIG. 1. As shown in FIG. 1, first, the mask for exposure 2 with the mask pattern formed thereon is mounted on the inspection apparatus (step S11). The image of the mask pattern formed on the mask for exposure 2 is taken in by the inspection apparatus (step S12), and the image data 3 is prepared (step S13). The deconvolution is performed based on the information of the optical system of the inspection apparatus (step S14), and the low-ordered diffracted light distribution generated by the mask pattern is obtained from the image data 3 (step S15). The exposure simulation in the optical system of the exposure apparatus is used, and the image intensity distribution of the mask pattern image obtained on the wafer is obtained from the low-ordered diffracted light distribution (step S16).

The simulation is used to obtain lithography margins of the mask pattern image transferred onto the wafer from the image intensity distribution (step S17). The lithography margins are margins of the depth of focus, exposure dose latitude, and the like with respect to the exposure conditions. When the obtained lithography margin has a magnitude over a predetermined reference, judgment results in OK. In this case, the mask for exposure is subsequently mounted on the exposure apparatus, and an exposure processing in a manufacturing process of the semiconductor device. On the other hand, when the obtained lithography margin is not more than the predetermined reference because of the defect of the mask pattern, the judgment results in NG (step S18). In this case, it is judged whether the defect can be corrected (step S19). When the defect can be corrected, the defect is corrected (step S20). Thereafter, the step returns to the step S12, and the processing of and after the step S12 is performed again. On the other hand, when the defect cannot be corrected, a new mask for exposure is redrawn and thereby formed (step S21).

FIG. 12 is a schematic diagram of the exposure apparatus for use in manufacturing the semiconductor device of the embodiment. A light from an exposure light source 10 goes via a reflective plate 10A, and an optical system 10B, and a light amount is adjusted by a σ diaphragm 11. The light whose light amount has been adjusted is transmitted through a mask for exposure 12 accepted by the inspection method of the embodiment. The light passed through the mask for exposure 12 is passed through a projection optical system 13 including an NA diaphragm 14 which has a predetermined value, and radiated onto a wafer 15 with a photo resist formed thereon. Moreover, the photo resist is exposed in a predetermined pattern. Thereafter, post-processes such as a developing process are performed, and the semiconductor device is formed.

In general, a numerical aperture (NAins) of an optical inspection apparatus is large as compared with a numerical aperture (NA) for use in the exposure apparatus. Moreover, for an inspection wavelength for use in the optical inspection apparatus, substantially the same wavelength as an exposure wavelength is increasingly used. This aims at enhancement of resolution of the inspection apparatus. Similarly as the projection optical system for use in the exposure apparatus, the image obtained by the inspection optical system is represented in the following equation using a partial coherent image forming theory.

$$I(x, y) = F^{-1}\left\{\int TCC(f, g; f', g')m(f, g)m*(f', g')df dg df' dg'\right\} \quad (8)$$

Additionally, F{ } denotes Fourier transform, F⁻{ } denotes Fourier reverse transform, and TCC denotes a transmission cross coefficient.

FIG. 13 shows an integration region of this equation.

$$TCC(f, g; f', g') = \int S(f'', g'')P(f + f'', g + g'')P*(f' + f'', g' + g'')df''dg'' \quad (9)$$

Additionally, S denotes an effective light source distribution, if $\sqrt{(f^2+g^2)} \leq \sigma_{ins}NA_{ins}/\lambda_{ins}$, S(f,g)=1, and Else S(f,g)=0. Moreover, σins denotes a coherence factor.

Moreover, P denotes a pupil function, if $\sqrt{(f^2+g^2)} \leq NA_{ins}/\lambda_{ins}$, |P(f,g)|=1, and Else P(f,g)=0. Moreover, m(f,g) is a diffracted light distribution obtained from the mask pattern, and is represented by $F^{-1}\{m(f,g)\}=m(x,y)$. Furthermore, m(x,y) denotes a complex amplitude transmittance distribution of the mask pattern.

The obtained mask pattern image I(x,y) is formed of a diffracted light which is transmitted through the mask pattern and which contains all components for use during actual exposure. Here, when the deconvolution is used, it is possible in principle to reconstitute the diffracted light distribution of the mask pattern from the obtained mask pattern image.

Details of the deconvolution will be described hereinafter.

The TCC represented by the equation (9) indicates transmission characteristics of the partial coherent optical system. Since the transmission characteristics obtained from this equation are band-limited, only low-ordered components of the diffracted light distribution for use in actual transfer contribute to the image formation.

FIG. 14 is a characteristic diagram showing the band of TCC(f,0;f',0). As seen from the above-described partial coherent image forming equation, the TCC is band-limited, and it is therefore apparent that the image intensity I(x,y) is not influenced by the diffracted light components outside the band.

That is, it is assumed that the exposure wavelength is λ, the numerical aperture of the projection optical system of the exposure apparatus is NA, and the coherence factor is σ. Moreover, as shown in FIG. 1, for the diffracted light distribution from the mask pattern for use during the exposure, assuming that a diffraction angle is θ, only the diffracted light of the following equation (10) contributes to the exposure.

$$-(1+\sigma)NA/\lambda \leq M \sin \theta \leq (1+\sigma)NA/\lambda \quad (10)$$

Additionally, 1/M denotes a mask reduction ratio. When the mask reduction ratio is 1/M, the mask pattern on the mask for exposure is reduced to 1/M and transferred onto the wafer.

Moreover, examples of a technique for obtaining the above-described m(f,g) include a technique of obtaining an initial value m0(f,g) from design data, assigning the value to the equation (10) to obtain the optical image I0(x,y), and perturbing and obtaining m(f,g) so as to minimize a difference between the optical image and the obtained inspection optical image I(x,y). Moreover, the examples also include a technique of developing the eigenvalue of the equation (10) according to an optimal coherent assumption (OCA) technique described in "Phase-shifting masks for microlithography: automated design and mask requirements" by Y. C. Pati, et al. in Journal of Optical Society of America A/Vol. 11, No. 9/pl. 2438–2452/September (1994), and using an obtained equation.

The image forming equation I(x,y) by the OCA is substantially represented as follows.

$$I(x,y) \sim F^{-1}\{\Sigma \sigma k((\phi k \cdot m(f,g)) \star (\phi k \cdot m(f,g)^*))\} \quad (11)$$

Additionally, σk denotes an eigenvalue in developing TCC with set of eigenfunction kernels Φk (k=0, 1, 1, 2, . . . , N) in an optimum manner, φk denotes Fourier transform of Φk, and ★ denotes correlation calculation. When this equation (11) is used, the speed of an optical image calculator is raised, and it is therefore possible to obtain the diffracted light distribution faster.

The NA, σ, and the like of the exposure apparatus, and parameters of the photo resist are appropriately given from the diffracted light distribution obtained in this manner, and the transfer simulation for transferring the mask pattern on the mask for exposure onto the wafer is performed. It is possible to perform the judgment more strictly by the simulation.

In comparison of the technique of extracting the contour of the conventional mask pattern to perform the simulation with the technique of the embodiment, when the technique of the embodiment of the present invention is used, the diffracted light distribution information of the mask pattern is directly obtained instead of the contour information. Therefore, it is possible to avoid a deviation from a scalar diffraction theory, and it is also possible to consider the influence by a defect of gray tone.

In the embodiment of the present invention, without inspecting the entire surface of the mask for exposure as described above, prospective error positions are first filtered and limited, so that a high-speed inspection processing can be achieved. In this case, it is preferable to appropriately combine the filtering technique with the conventional inspection technique. That is, in the above-described die to DB and die to die techniques, the detection sensitivity is strictly set, and the technique according to the embodiment of the present invention is applied, so that the number of simulations can be reduced, and higher-speed processing is enabled.

Additionally, in the preferred embodiment of the present invention, the inspection wavelength for use in the inspection apparatus is preferably substantially the same as the exposure wavelength for use in the exposure apparatus. Alternatively, it is preferable to set the inspection wavelength in a range in which optical characteristics of optical components of mask for exposure, (substrate(Qz), shield member(Cr, MoSi, etc), and the like), and materials for the process (resist for patterning the mask pattern, and the like) for forming the mask pattern as a defect factor do not change a lot as compared with the use of the exposure wavelength, or can be converted.

Moreover, for the resolution (element size) of an image intensity monitor element for monitoring the image intensity distribution of the detection optical system for use in the embodiment of the present invention, the resolution needs to be smaller than at least ½ of an inverse number of a cutoff frequency (vc≤(1+σins)NAins/λins) determined by NAins, λins of the inspection optical apparatus. Since the exposure apparatus optically functions as a type of a low pass filter, the image obtained via the detection optical system is band-limited in a space frequency manner. It is possible to reconstitute the image in an optional space coordinate position from sampled data finer than ½ of the inverse number of the cutoff frequency according to the sampling theorem shown in FIG. 2.

Moreover, for capabilities of the image intensity monitor element, it is preferable to use the element broad in range, multiple in scale, and superior in linearity. The element preferably has a resolution of an intensity direction of at least 256 or more scales in a range in which saturation does not occur during measurement.

Furthermore, as means for performing acceptance/rejection judgment after the inspection, as shown in FIG. 9, it is preferable to calculate and obtain the exposure dose latitude and depth of focus, and to judge whether the necessary margin can be secured.

According to the embodiment of the present invention, the inspection wavelength substantially equal to the exposure wavelength for use in exposure is used, and an image is thereby obtained in which the transmittance distribution of the mask for exposure is accurately reflected. Additionally, the NA of the objective optical system of the inspection apparatus, which is larger than the NA of the projection optical system in the exposure optical system, is used. Then, the obtained image contains all the components of the diffracted light distribution for use during the exposure. Therefore, when the image intensity distribution obtained by the inspection optical system is subjected to the deconvolution, it is possible to reconstitute the diffracted light distribution obtained from the mask pattern. Furthermore, when the diffracted light distribution is used to execute the exposure simulation, the defect present on the mask for exposure can be transferred with a high precision.

A preferred embodiment of the present invention will be described hereinafter.

According to the embodiment of the present invention, there is provided an inspection method of a mask pattern for exposure for use in an exposure apparatus for manufacturing a semiconductor device, comprising: a step of using substantially the same inspection wavelength as an exposure wavelength for use in the exposure apparatus and using a detection optical system of the inspection apparatus having a numerical aperture larger than the numerical aperture of a projection optical system of the exposure apparatus to prepare image data of the mask pattern for exposure using the detection optical system; a step of reconstructing low-ordered diffracted light distribution obtained from the mask pattern for exposure by using the image data based on information of the detection optical system; a step of using transfer simulation in the projection optical system of the exposure apparatus to obtain an image intensity distribution obtained on a wafer from the low-ordered diffracted light distribution; and a step of comparing the obtained image intensity distribution with the image data to judge acceptance/rejection of inspection.

The inspection wavelength (λins) may be set in a range in which the optical characteristics during the use of the exposure wavelength (λ) and the optical characteristics during the use of the inspection wavelength do not substantially change. Furthermore, the inspection wavelength (λins) having the range of the following equation (1) with respect to the exposure wavelength (λ) may be used.

$$0.9\lambda \leq \lambda ins \leq 1.1\lambda \tag{1}$$

Moreover, for the image data of the mask pattern for exposure, a pixel distance (D) converted on the mask to be inspected of the image data may satisfy at least a condition of the following equation (2).

$$D \leq \lambda ins/(2(1+\sigma ins)NAins) \tag{2}$$

Additionally, λins denotes the inspection wavelength, NAins denotes an objective side numerical aperture of the detection optical system, and σins denotes the coherence factor of the detection optical system.

Moreover, for the diffracted light distribution, only the diffracted light distribution present in the range of the following equations (3), (4) may be used as the low-ordered diffracted light distribution (m(f,g)) of the mask pattern.

$$-(1+\sigma)NA/\lambda \leq f \leq (1+\sigma)NA/\lambda \tag{3}$$

$$-(1+\sigma)NA/\lambda \leq g \leq (1+\sigma)NA/\lambda \tag{4}$$

Additionally, σ denotes the coherence factor of the exposure apparatus, NA denotes the projection optical system numerical aperture of the exposure apparatus, λ denotes the exposure wavelength, and f, g denote the projection optical system pupil coordinate of the exposure apparatus.

Moreover, for the diffracted light distribution of the mask pattern for exposure, the initial value (m0(f,g)) of the diffracted light distribution obtained from the design value of the mask pattern for exposure may be perturbed and the value of m(f,g) may be obtained so as to minimize the value of R obtained by the following equation (5).

$$R(m) = \int \Big[ I(x, y) - \tag{5}$$
$$F^{-1}\Big\{\int TCC(f, g; f', g')m(f, g)m*(f', g')dfdgdf'dg'\Big\}\Big] dxdy$$

Additionally, $F^{-1}\{\ \}$ denotes Fourier reverse transform, and TCC denotes a transmission cross coefficient.

Moreover, the diffracted light distribution (m(f,g)) of the mask pattern for exposure may be obtained from data (I(x,y)) obtained by correcting the obtained image data in the light intensity distribution in the detection apparatus surface of the detection optical system so as to minimize the value of R determined by the following equation (6).

$$R(m) = \int \Big[ I(x, y) - F^{-1}\Big\{\sum \sigma k((\phi k \cdot m(f, g)) \star (\phi k \cdot m(f, g)^*))\Big\} dxdy \tag{6}$$

Additionally, $F^{-1}\{\ \}$ denotes Fourier reverse transform, φk denotes a function core obtained by developing the transmission cross coefficient (TCC) in the eigenvalue by the optimal coherent assumption (OCA), σk denotes the eigenvalue, and ★ represents the correlation calculation.

Moreover, to perform the acceptance/rejection judgment of the inspection, a predetermined focusing precision during exposure or an exposure amount dispersion is assumed, a processed shape obtained on the wafer under the conditions is obtained, and it may be judged whether the dimension precision satisfies the predetermined reference.

Furthermore, the inspection method of the mask pattern for exposure is used to form the photo mask for exposure. Moreover, the photo mask for exposure is used in the manufacturing process and the semiconductor device is manufactured.

As described above, in the embodiment of the present invention, it is possible to more strictly obtain the transfer property of the defect directly from the mask pattern image, and the allowable defect size can more strictly be obtained. As a result, there is provided the inspection method of the mask pattern formed on the mask for exposure in which the allowable value of the defect can be moderated.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An inspection method of a mask pattern for exposure for use in an exposure apparatus for manufacturing a semiconductor device, comprising:

using substantially the same inspection wavelength as an exposure wavelength for use in said exposure apparatus and using a detection optical system of said inspection apparatus having a numerical aperture larger than a numerical aperture of a projection optical system of said exposure apparatus to prepare image data of said mask pattern for exposure using the detection optical system;

reconstructing a low-ordered diffracted light distribution obtained from said mask pattern for exposure by using the image data based on information of said detection optical system;

using transfer simulation in said projection optical system of said exposure apparatus to obtain an image intensity distribution obtained on a wafer from the low-ordered diffracted light distribution; and judging acceptance/rejection of inspection based on said obtained image intensity distribution.

2. The inspection method of the mask pattern for exposure according to claim 1, further comprising: setting said inspection wavelength ($\lambda$ins) in a range in which optical characteristics during the use of said exposure wavelength ($\lambda$) and optical characteristics during the use of said inspection wavelength do not change.

3. The inspection method of the mask pattern for exposure according to claim 2, further comprising: using said inspection wavelength ($\lambda$ins) which has the range of the following equation (1) with respect to said exposure wavelength ($\lambda$):

$$0.9\lambda \leq \lambda ins \leq 1.1\lambda \qquad (1).$$

4. The inspection method of the mask pattern for exposure according to claim 1, further comprising: preparing said image data of said mask pattern for exposure so that a pixel distance (D) converted on the mask to be inspected of the image data satisfies at least a condition of the following equation (2):

$$D \leq \lambda ins/(2(1+\sigma ins)NAins) \qquad (2),$$

in which $\lambda$ins denotes said inspection wavelength, NAins denotes an objective side numerical aperture of said detection optical system, and $\sigma$ins denotes a coherence factor of said detection optical system.

5. The inspection method of the mask pattern for exposure according to claim 1, wherein obtaining said low-ordered diffracted light distribution comprises: using only the diffracted light distribution present in the range of the following equations (3), (4) as said low-ordered diffracted light distribution (m(f,g)) of the mask pattern:

$$-(1+\sigma)NA/\lambda \leq f \leq (1+\sigma)NA/\lambda \qquad (3); \text{ and}$$

$$-(1+\sigma)NA/\lambda \leq g \leq (1+\sigma)NA/\lambda \qquad (4),$$

in which $\sigma$ denotes a coherence factor of said exposure apparatus, NA denotes a projection optical system numerical aperture of said exposure apparatus, $\lambda$ denotes said exposure wavelength, and f, g denote a projection optical system pupil coordinate of said exposure apparatus.

6. The inspection method of the mask pattern for exposure according to claim 5, wherein obtaining said diffracted light distribution of said mask pattern for exposure comprises: perturbing an initial value (m0(f,g)) of the diffracted light distribution obtained from a design value of said mask pattern for exposure and obtaining a value of m(f,g) so as to minimize the value of R obtained by the following equation (5):

$$R(m) = \int \left[ I(x, y) - F^{-1}\left\{ \int TCC(f, g; f', g')m(f, g)m*(f', g')dfdgdf'dg' \right\} \right] dxdy, \qquad (5)$$

in which $F^{-1}\{\ \}$ denotes Fourier reverse transform, and TCC denotes a transmission cross coefficient.

7. The inspection method of the mask pattern for exposure according to claim 5, further comprising: obtaining said diffracted light distribution (m(f,g)) of said mask pattern for exposure from data (I(x,y)) obtained by correcting said obtained image data in a light intensity distribution in a detection apparatus surface of said detection optical system so as to minimize the value of R determined by the following equation (6):

$$R(m) = \int [I(x, y) - F^{-1}\{\sum \sigma k((\phi k \cdot m(f, g)) \star (\phi k \cdot m(f, g)^*))dxdy, \qquad (6)$$

in which $F^{-1}\{\ \}$ denotes Fourier reverse transform, $\phi k$ denotes a function core obtained by developing the transmission cross coefficient (TCC) in an eigenvalue by optimal coherent assumption (OCA), $\sigma k$ denotes the eigenvalue, and ★ represents correlation calculation.

8. The inspection method of the mask pattern for exposure according to claim 1, wherein performing said acceptance/rejection judgment of said inspection comprises: assuming a predetermined focusing precision or an exposure amount dispersion during exposure; obtaining a processed shape obtained on the wafer under the conditions; and judging whether a dimension precision satisfies a predetermined reference.

9. A photo mask for exposure which is formed using the inspection method of the mask pattern for exposure according to claim 1.

10. A semiconductor device which is manufactured using a photo mask for exposure formed using the inspection method of the mask pattern for exposure according to claim 1 in a manufacturing process.

* * * * *